United States Patent [19]
Hengstenberg et al.

[11] Patent Number: 5,672,470
[45] Date of Patent: Sep. 30, 1997

[54] MICROBIAL PROCESS FOR DETECTION OF TOXIC SUBSTANCES

[76] Inventors: Wolfgang Hengstenberg, Universitätsstr. 150, 44789 Bochum; Roman Kolar, Kohlenbankstr. 18, 44227 Dortmund; Marko Scholz, Hunscheidtstr. 43, 44789 Bochum, all of Germany

[21] Appl. No.: 375,818

[22] Filed: Jan. 20, 1995

[30] Foreign Application Priority Data

Jan. 22, 1994 [DE] Germany .................. 44 01 868.1

[51] Int. Cl.$^6$ .................................. C12Q 1/02
[52] U.S. Cl. .................................. 435/4; 435/29
[58] Field of Search .................. 435/29, 30, 34, 435/4

[56] References Cited

U.S. PATENT DOCUMENTS 4,932,871  6/1990  Bell et al. .................. 435/97
5,149,652  9/1992  Bittoy .................. 435/29

FOREIGN PATENT DOCUMENTS 286039   10/1988  European Pat. Off. .
2005018  4/1979   United Kingdom .

OTHER PUBLICATIONS

Shavma et al. Journal of Biological Chemistry vol. 268 No. 24 pp. 17695–17704.
G. Tesoriere et al. "The Purification and Properties of Nucleoside Phosphotransferase From Mucosa of Chicken Intestine", 231–244, 1984, Biochimica et Biophysica Acta.
V.L. Crow et al. "The Effect of Monovalent and Divalent Cations on the Activity of Streptococcus Lactis C10 Pyruvate Kinase", 105–114, 1977, Biochimica et Biophysica Acta. L. Ciskanik et al. Inhibition and Inactivation of Pyruvate Phosphate Dikinase with Cr(III).
"Complexes of Adenosine 5'–Triphosphate and Inorganic Pyrophosphate", 113–125, 1986, J. Enzyme Inhibition, vol. 1.
I.A. Brand et al. "Zn2+-dependent Reversible Inactivation of Rat Liver Phosphofructokinase-1", 5892–5900, 1986, The Journal of Biological Chemistry.

*Primary Examiner*—Carolyn Paden
*Attorney, Agent, or Firm*—Mary R. Bonzagni, Esq.; Holland & Bonzagni, P.C.

[57] ABSTRACT

A microbial process for detection of toxic substances. The bacterial luminescence test so far used to detect toxic substances is extremely fast in its performance and reacts with very high sensitivity to heavy metals such as mercury and lead. However, that is not the case for other toxicologically relevant heavy metals such as cadmium and chromium. The inhibitory effect of toxic substances on the phosphotransferase system of bacteria, in particular, the *E. coli* mutant 1219 bgl+, is set forth as proof for the presence of toxic substances in samples. This test method responds with high sensitivity to the presence of the heavy metals cadmium and chromium. The test process constitutes a complement to the bacterial luminescence test and makes it possible to quickly exclude the presence of toxicologically relevant concentrations of cadmium and chromium in such cases where only a slight or no effect at all is indicated on the phosphotransferase system.

14 Claims, 2 Drawing Sheets

MICROBIAL PROCESS FOR DETECTION OF TOXIC SUBSTANCES

FIELD OF THE INVENTION

The invention concerns a microbial process for detection of toxic substances, particularly in heavy metals by determining the effect of such toxic substances, contained in a sample, on the metabolism of microorganisms.

BACKGROUND OF THE INVENTION

Multiple biotests for the demonstration of toxic substances are known in the State of the Art. The requirements on such biotests are numerous, such as for example standardization, lasting availability, reproducibility, high sensitivity or low indication or detection limit, rapid speed and problem-free handling, low-cost implementation and, not the least, a reliable correlation of the measured effects to biological processes. Therefore, these requirements as a whole bring about further problems relative to the credibility of the declared evidence of the measured test results. For instance the requirements on rapid speed along with minute detection limit and a high reproducibility often exclude each other mutually. In addition, certain environmental chemicals are toxic with respect to one organism, but not to the other one. That's why, in the field of effluents treatment, there are biotests with different DIN-Norm that are performed with organisms of a different organizational level. The test organisms used are identified in TABLE 1 hereinbelow and are in each case to represent the most important organisms in surface waters.

TABLE 1

| BIOTEST | TEST ORGANISM | ASSAY PARAMETER |
|---|---|---|
| Fish test DIN 38412, Part 31 | Goldorfe (kind of carp fish) Leuciscus idus | LCO: max. Concentration leading to 0% mortality after 48 h. of incubation |
| Daphnien test DIN 38412, Part 30 | Water flea Daphnia magna | GD: smallest dilution stage at which 90% of the test animals retain their buoyancy or swimming ability |
| Algae test DIN 38412, Part 33 | Green alga Scenedesmus subspicatus | HF: Inhibition effect of the chlorophyll-fluorescence on the biomass production in % |
| Bacterial luminescence test DIN 38412, Part 34 | Bacteria Vibrio fischen | EC20: max. Concentration leading to 20% inhibition of photo emission after 20 min. of incubation |

These biotests, however, are not to be looked upon as alternative tests. Because the single organisms respond to a respective toxic substance or a combination of toxic substances both with different sensitivity and with different specificity, intelligent statements about a toxic substance potential present in each sample or about the general pernicious capacity thereof can be made from these tests only in combination with each other before single toxic substances in the sample are individually determined quantitatively.

In Table 2, there is for example shown an ecotoxicological test program with different biological test parameters as proposed by Bundesumweltamt, the German Environmental Agency. The single biotests differ in costs both with respect to equipment and time. The effect of the toxic substances, in particular in the Goldorfen, Daphnien and Green alga tests is focused on the long-term effect of the entire organism on the acting toxic substances. Therefore such test methods require a relatively large time consumption. In addition, fish tests as an example require a relatively complex and expensive handling of the test organisms.

TABLE 2

ECOTOXICOLOGICAL TESTS AT THE ELEMENTARY STAGE AND STAGE 1

| TEST METHOD | TEST PARAMETER | TEST ORGANISMS |
|---|---|---|
| Elementary stage | | |
| Acute toxicity in one species of fish | Deathly effect of the substance after 1-time application during 24-48 hours | Zebra danio Brachdydanio rerio Secondary consumer |
| Acute toxicity in one species of water fleas | Inhibition of buoyancy or swimming ability after 1-time application during 24-48 hours | Large water flea Daphnia magna Primary consumer |
| Stage 1 | | |
| Algae toxicity | Inhibition of cell multiplication (growth) after 1-time application during 72 hours | Green alga Scenedesmus subspicatus Primary producer |
| Long-term Daphnien toxicity | Ascertainment of No-Observed-Effect-Concentration and of threshold concentration with respect to an adverse effect on reproduction performance and deathly effect after reiterated (semistatic) or constant (through-flow system) application during at least 21 days | Large water flea Daphnia magna |
| Long-term fish toxicity | Ascertainment of No-Observed-Effect-Concentration and of threshold concentration with respect to deathly and sublethal effects after reiterated (semistatic) or constant (through-flow system) application during 14-28 days | Zebra danio brachydanio rerio |
| Plant toxicity | Inhibition of growth of seed for sowing (reduction of the biomass) during 14 days after 1-time application | Oats Avena sativa Turnip Brassica rapa Primary producer |
| Earthworm toxicity | Deathly effect of the substance during 14 days after 1-time application | Earthworm Eisenia foetida Secondary destructor |
| Stage 2 | | |
| Individual substance-specific test program | | |

It is possible to achieve much faster results at less efforts and costs employing the so-called "acute biotests" with use of microorganisms. The effect on one toxic substance will thereby be determined only across one measurable parameter of an organism, which can be correlated with the "effective concentration" (EC value) as a toxicological, characteristic quantity.

For example, the bacterial luminescence test described in DE-PS 28 41 896 is a process with which, for the purpose of detecting a toxic substance or a toxic condition, the change in photoemission deriving from a bioluminescence organism is determined as a measure of the action of the toxic substance on, or the toxic condition of, the metabolism of the bioluminescence organism. Such a microbial test can be carried out extremely fast (a couple of minutes) in comparison to a biological test with eukaryotes. However, since a prokaryotes is used, the microbial test has the disadvantage of not easily achieving a correlation of the observed toxic substance effect to, in turn, their effect on eukaryotes.

It has been demonstrated, however, that the microorganisms used in a bacterial luminescence test respond extremely sensitively and specifically to the toxic heavy metals mercury and lead. This now offers the advantage that it can be extremely fast ascertained, in pre-testing, whether or not precisely these heavy metals are included in a sample as toxic substances. Given a negative result in the bacterial luminescence test, the presence of mercury and lead in toxicological amounts can then be excluded beforehand within minutes.

The fact is however that with the bacterial luminescence test, which so far is the only known bacterial test, there are two additional very important toxic heavy metals, cadmium and chromium, the presence of which cannot be ascertained or the test is not responsive thereto with sufficient sensitivity. This is in particular the case with cadmium, which is included as $CdCl_2$ at No. 22 on the list over substances of the "25-substance-program" issued by Bundesgesundheitsamt, the German Health Agency.

It is therefore the objective of the invention to provide a further bacterial test, with which the presence of the toxic heavy metals cadmium and chromium can be ascertained in a sample with such high sensitivity and specificity, that, upon non-response of the test system, the presence of cadmium and chromium as to toxicological concentrations in the sample can be excluded.

SUMMARY OF THE INVENTION

That objective will be achieved in that the inhibition effect of the toxic substances on the bacteria phosphotransferase system (PTS) will be brought forth as evidence for the presence of toxic substances in the sample. Advantageous embodiments are represented in the independent claims.

DETAILED DESCRIPTION OF THE INVENTION

The bacteria phosphotransferase system is a multienzyme complex and constitutes an essential element in providing energy in bacteria. It consists of the Enzyme I (EI) and the HPr (heat stable protein/histidine protein) building components, which are localized in the cytoplasm, is unspecific in relation to carbohydrates and expressed in a constitutive manner. Further building components are constituted by the carbohydrate specific Enzymes II (EII), which are inducible and represent a heterogenous group with a variable arrangement of their functional domains. For the E. coli, the following arrangements can be given as examples:

1. The Mannitol-PTS consists of one single, membrane-bound protein that is composed of the three A, B and C domains: IIABC.
2. The Glucose-PTS consists of two or more proteins, of which one is in dissolved form with one domain, and the other one is membrane-bound having two domains: IIA, IICB.
3. In Mannose-PTS, the IIA and IIB are fusioned as singular cytoplasm-soluble polypeptides, the sugar translocation occurs across the membrane by means of two integral membrane proteins—namely, IIC and IID.

In any case, the phsophoryl group tansfer starting out from phosphoenol pyruvate (PEP) takes place via EI, Hpr, IIA and IIB. The IIC domain represents the integral membrane portion, which constitutes the transport channel and has the sugar specific binding site.

Besides the above-described phosphotransferase systems for glucose, mannose and mannitol other, less frequent organization forms appear in other species of microorganisms.

The EI of the PTS is phosphorylated by PEP at the N3 position of a histidyl residue. The phosphorylation occurs in the dimer form of the protein, each monomer carrying a phosphoryl group.

The phosphorylation of the Hpr by phosphorylated EI occurs at the N1 position of a histidyl residue (His 15 in E. coli). Continued transfer of the phosphoryl group then occurs, with starting point from phosphorylated Hpr, on carbohydrate specific domains, which exist as a very heterogenous group. Most EII have the three domains: IIA, IIB and IIC. IIA and IIB represent the hydrophilic domain, and IIC (and/or IID) the lipophilic domain. While essential importance is assigned to the IIA and IIB domains when transferring phosphoryl groups, the IIC and IID domains, respectively, represent the carbohydrate recognition site and the transmembrane channel. From the phosphorylated Hpr the phosphoryl group will initially be transferred onto a histidyl residue of the IIA domain. There is presently less information available from the hydrophilic IIB domains, which take part in the phosphoryl group transfer via cysteyl groups. The IIC domains repeatedly span through the cell membrane as helices. The configuration of the transmembrane channel occurs possibly through oligomerization of several IIC's of the corresponding EII proteins so as to provide a sufficient number of amphipatic alpha-helices.

Since the phosphotransferase system for the bacterial cell is an essential transport system for the reception of extracellular carbohydrates, a possible inhibition or adverse effect of the participating enzymes should be noticed to cause a reduction in the carbohydrate transport, that is the PTS constitutes a potential possibility for the detection of toxic substances in microorganisms. It is known that toxic substances such as organic solvents or detergents inhibit enzyme activities. This is in particular the case for heavy metals, which are considered to be strong enzyme inhibitors. According to this invention, a substrate analog has now been introduced into the transport through the cell membrane instead of a carbohydrate. Said analog is of such a nature that it, in phosphorylated form after the cell transport, can be hydrolyzed by an enzyme in the bacterial cell under the release of a substance susceptible to analysis. If, for instance, 2-nitrophenyl-β-D-glucoside is used as substrate analog, this will be channeled by the PTS under phosphorylation into a bacterial cell, where the ONP-Glc-6-P is broken down hydrolytically by the inducible 6-phospho-β-glucosidase B to Glc-6-P and 2-nitrophenyl. The released 2-nitrophenyl can then, by means of photometry, be quantitatively measured as phenolate-anion after a defined time span. Additionally, with E. coli mutant 1219bgl+ a bacterium is present that is characterized by increased β-glycoside activity, yet is not transformed through genetic engineering nor is pathogenic, which is an important prerequisite for harmless work with bacteria.

The performance of a PTS inhibition test will now be described below.

The optimal reaction parameters given below relate to the use of the E. coli mutant 1219bgl+ deposited Sep. 22, 1993 with the following depository: DSM-DEUTSCHE SAMMLUNG VON MIKROORGANISMEN UND ZELLKULTUREN GmbH, Mascheroder Weg 1b, D-38124 Braunschweig, and given accession number DSM 8779. For the purpose of optimization, when using other strains of bacteria with PTS, values which may deviate from case to case have to be set for the reaction parameters, and those values would have to be established in pre-testing.

BRIEF DESCRIPTION OF THE DRAWINGS

In FIGS. 1–4, the functional contexts of some parameters are represented. It is shown in:

FIG. 1: The dependency of the degree of hydrolysis (in % of residue activity) of ONP-glucose in $E.\ coli$, on the concentration of the bovine serum albumin solution, in which the bacteria were washed.

FIG. 2: The dependency of the transformation of ONP-glycoside on the pH value.

FIG. 3: The temperature dependency of the transformation of ONP-glycoside.

FIG. 4: The dependency of the ONP-glycoside cleavage on the substrate concentration.

Figure 1:
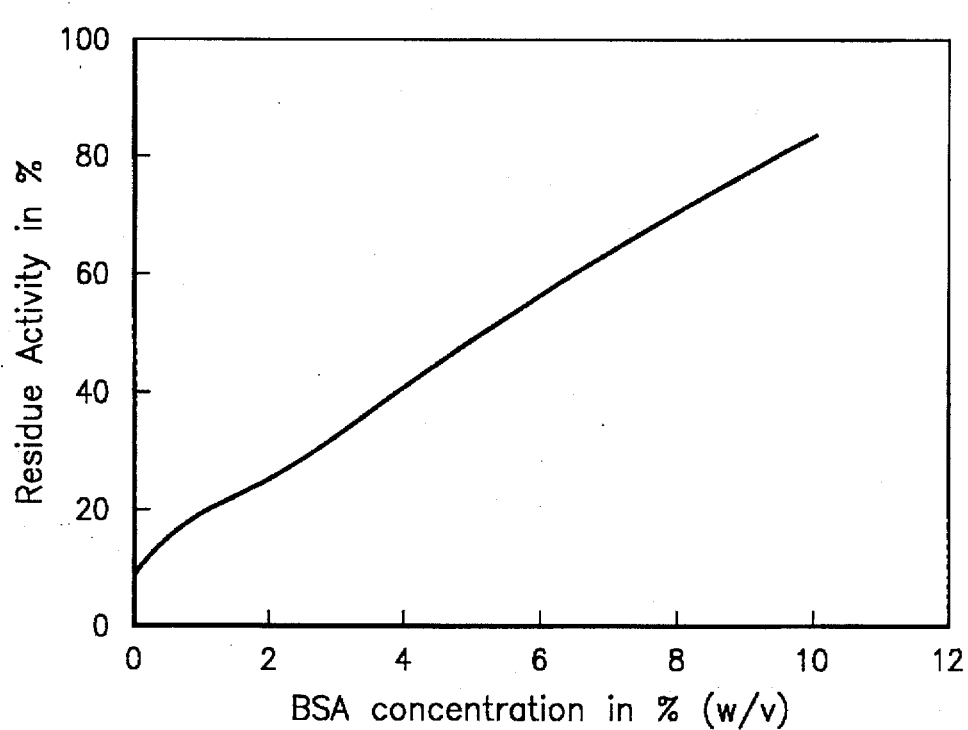

Before using the bacteria these must be examined on an intact PTS. Cells of the appropriate bacteria strain is for this purpose dispersed on UMB selective plates and bred at 30° C. (UMB=4-methylumbelliferone as fluorescence indicator). The manufacture of the UMB selective plates is carried out with 15 g of agar, 25 ml of salicin (20% w/v), which induces the β-glucoside-PTS and serves as test substrate for β-glycosidases, and both are filled to 1,000 ml with TBY-medium. The TBY-medium is composed of 10 g Trypton, 5 g yeast extract, 5 g NaCl which all together were filled to 1,000 ml with distilled water. In case carbohydrates are required to cultivate the bacteria, they are separately autoclaved and brought, upon cooling under sterile conditions, to a final concentration of 0.5% (w/v). 50 ml of UMB-β-D-glucoside (1 µg/ml DMSO) are then dispersed onto the agar plates.

The UMB-glucose serves as substrate analog to salicin. Salicin is a test substrate for β-glycosidases and is transported into the cell and phosphorylated through the PTS. Similar thereto, the UMB-glucose is then phosphorylated to UMB-Glc-6-P and, after that, hydrolyzed by the inducible 6-phospho-β-glucosidase B to glucose-6-P and UMB. Due to its fluorescent property, the released UMB, upon excitation with light at a wavelength of 365 nm, serves as a fluorescent indicator for an intact PTS.

In order to have test bacteria available when needed in an expeditious way and to a sufficient amount, a storage of conserved cells must be arranged in advance. For the purpose, the above described TBY medium is inoculated with a tenth of the volume of a colony of bacteria of the appropriate strain, and bred at 30° C. (for instance in a circular shake apparatus at 180 rotations/min). The induction of the bgl-PTS in the case of $E.\ coli$ 1219 occurs through the immediate addition of salicin into the medium to reach a final concentration of 0.5% (w/v).

The cell growth is checked by measuring the O.D. (optical density) at 578 nm, the induction of the PTS by measuring the O.D. at 405 nm after induction with ONP-β-D-glucoside (instead of and representing 2-nitrophenyl-β-D-glucoside (ONP-glucoside), 4-nitrophenyl-µ-D-glucoside may also be used, although this has not been mentioned in the following embodiments. If the cells in the dispersion have reached an $O.D._{578}$ of 2.0, cells are yielded from a 10 min centrifugation at 17,000×g (in the case of large volumes, after 20 min with 11,000×g).

The pH value is then set at pH 6.5 after application of 50 mM of a physiologically useable buffer, which is always used, and the PTS test should always be performed. Preferably, one of the following should be considered as buffers:

HEPES buffer (50 mM) with NaOH set at pH 6.5–7.5.
Bis/Tris buffer (50 mM) with HCl set at pH 6.5.
tris/HCl buffer (50 mM) with HCl set at pH 6.5.
Phosphate buffer: Solution A: $Na_2HPO_4$ (50 mM, 100 mM); Solution B: $KH_2PO_4$ (50 mM, 100 mM). Solution A is given first, the Solution B (same concentration) being set at the appropriate pH value.

In particular, HEPES buffer and phosphate buffer are the preferred ones.

Preservation of the bacteria cultures is preferably done by freezing. For that purpose the cultivated bacteria cultures described above must undergo a pre-treatment. Since, due to the cell wall structure of Gram-negative bacteria with a simple murein sacculus, it is not that easy to freeze the $E.\ coli$ cells, because the ice crystals that occur upon cooling below freezing point would ruin the cell wall, the bacteria would have to dissolve in a rethawing procedure. This can be demonstrated, in $E.\ coli$ cultures, in conjunction with the low ONP-glucose-transformation rates of the bacteria cells that were thawed without a pretreatment. The remaining ONP-formation of the earlier frozen bacteria then amounts only to 16% relative to the transformation of the cells before the preservation procedure. It turned out that the reactivation of the rethawed bacteria cells depends on the washing process before freezing. It turned out, furthermore, that during washing with BSA solutions (bovine serum albumin) the increase of the residue activity in the measured area rose proportionally to the BSA concentration of the solution (with residue activity is meant the quotient of the substrate transformation before and after freezing). For the demonstration thereof, $E.\ coli$ cells were initially washed in one twentieth of volume of different aqueous solutions (Table 3) and frozen at −20° C. An evaluation occurred, where the quotients of the hydrolysis of the ONP-glucose of the bacteria were established with the aid of the PTS test after thawing and before freezing. Hereby it was possible to make statements with regard to survival rate of the bacteria in % residue activity. In Table 3, there is shown the percentage residue activities of the transformation of the ONP-glucose, which was achieved through the bacteria.

TABLE 3

| Test solution | Glycerin (88%) | BSA (1%) | BSA (10%) | Glycerin (44%) $MgCl_2$ (50 mM) |
|---|---|---|---|---|
| Residue Activity | 40.9% | 26.6% | 85% | 55% |

| Test solution | $MgCl_2$ (50 mM) NaCl (20 mM) | BSA (0.5%) Glycerin (44%) | BSA (0.5%) $MgCl_2$ (50 mM) | Cell pellet without additive |
|---|---|---|---|---|
| Residue Activity | 15.6% | 51.3% | 14.3% | 16% |

As can be seen from Table 3, high residue activity is achieved by using BSA solutions of high concentrations. It is also obvious that other additives are not needed for the preservation. It is clearly appreciated that, in the measured concentration area, the hydrolysis of the ONP-glucose of $E.\ coli$ is proportional to the concentration of the BSA solution, in which the bacteria were previously washed (FIG. 1).

It can also be viewed that the residue activity of the bacteria, after rethawing, is independent of the freezing method employed. To this aim, the microorganisms, which were washed in a 10% BSA solution, were submersed for freezing at −20° C. and −80° C. in a deep-freeze receptacle, and for shock freezing for 30 sec. into a mixture bath of dry ice/acetone (−78° C.) and into liquid nitrogen (−196° C.), respectively, and then stored at −20° C. and −80° C., respectively. The freezing methods described did not show any differences in regard to the percentage residue activity.

According to the invention, the cells of the *E. coli* mutant 1219bgl+ are therefore washed for preservation after their yield in a twentieth volume of BSA solution (10%), divided up in doses and stored through freezing at −20° C. In that way they will be available in variable quantities for subsequent tests. The mean residue activities, according to the present process, amount to approx. 85% (Table 2); It was also possible to reach this value after 6 months of storage at −20° C.

For use of the *E. coli* cultures preserved at −20° C., these must first be reactivated by thawing for 10 minutes at room temperature.

For the subsequent inhibition test the microorganisms must be incubated, before the actual start of the reaction, with the test solution (ONP-glucose) in a suitable buffer system. During the effective reaction time the ability of the cells to hydrolyze the ONP-glycoside should not decline. It has turned out that, for *E. coli*, an incubation time of 10–15 minutes at a temperature of 37° C. will render the best results. For species of microorganisms a temperature adaptation occurs during this time span. It could be demonstrated in pre-testing that, after the adaptation of temperature, an ONP-glucose transformation which increased by approx. 13% was registered. It remained constant for approx. 60 minutes. This is in particular advantageous, since the ability of the cells to hydrolyze ONP-glycoside should not decline in the course of the reaction time span. These state of affairs have to be understood. Otherwise it is not possible to know if a reduced ONP formation was caused by consumed energy reserves or though incubation with the toxic substances. If the ONP-glycoside hydrolysis is pursued at 37° C. without pre-incubation, it will be found that not until after 15 minutes will the maximal ONP-glucose cleavage of approx. 194 nmol/ml be achieved, which corresponds to an increase by 12.9%. The transformation rate will now remain constant between 15 and 45 minutes, and will then be diminishing by about 13% for up to approx. 90 minutes after reaction start.

In order to obtain exact and reproducible data for the subsequent PTS inhibition test, the reaction parameters must be optimally adapted to each other. Because of the substrate transformation being proportional to the reaction time and to the bacteria amount used, a compromise was made for the combination of both assay parameters. The compromise provides for a moderate transformation rate in a short time. For a volume of 500 µl at 37° C., the reaction time of the incubation batch is, according to the invention, preferably 5 minutes at an O.D.$_{578}$ of 3.0 for the cell suspension. The number of cells recorded by a Neubauer count chamber, for the *E. coli* mutant 1219 bgl+ amounted to 2.2×10$^{10}$ cells/ml.

Figure 2:
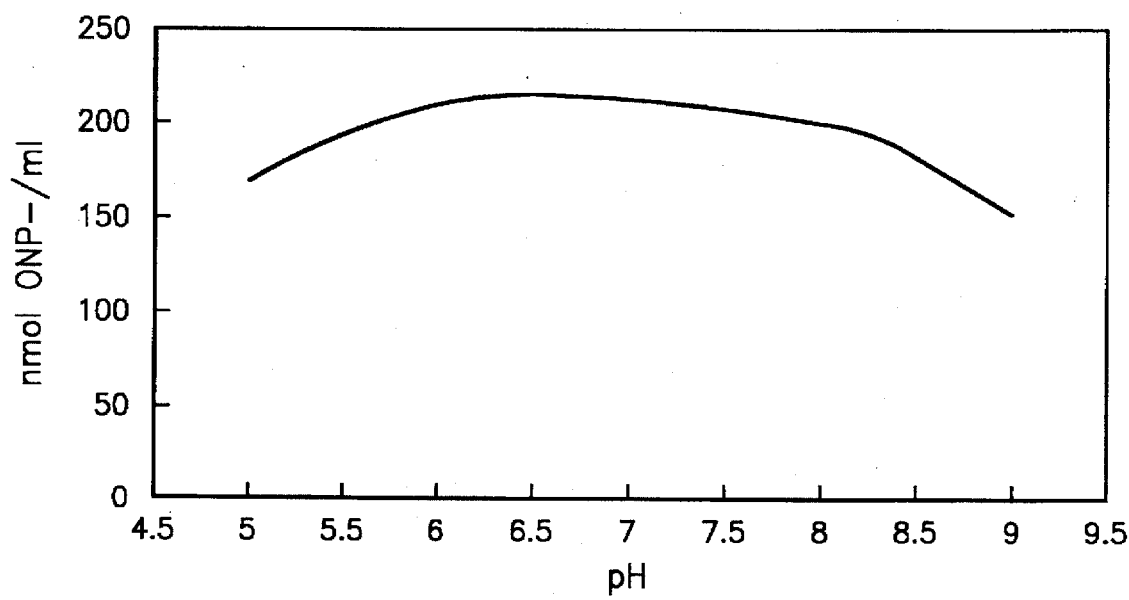

If one follows the ONP-glycoside transformation in dependency on pH value of the buffer system in a range between pH 5.0 an pH 9.0, it is noted that the transformation for *E. coli* remains relatively constant within a broad pH range of pH 5.5–pH 8.5, whereas the ONP-glucose cleavage rate rapidly diminishes at a pH value over 8.5. (FIG. 2). Thus, with *E. coli* 1219 a bacteria strain is available, which is useable in a broad pH area and, in addition, only needs a short reaction time (a 10–15 minute pre-incubation and a 5 minute reaction duration). For the PTS inhibition test according to the invention, a pH value of 6.5 is preferably set.

Figure 3:
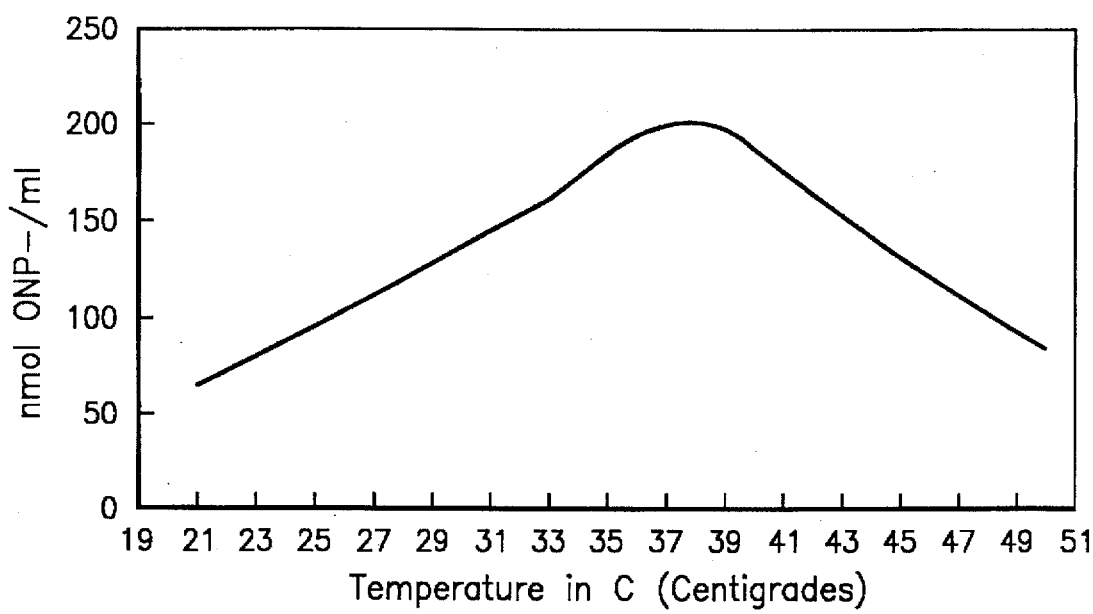

If one follows the temperature dependency of the ONP-glycoside hydrolysis between 21° C. and 50° C., it is noted that a maximum can be found at approx. 39° C. and that for further temperature increase the hydrolysis rate will rapidly decrease (FIG. 3). Because the ONP-glycoside hydrolysis rate at a temperature of 37° C., which is generally used in laboratories for physiological assays, is only slightly lower than at a maximum point of 39° C., a temperature of 37° C. is chosen for the inhibition test according to the present invention.

Figure 4:
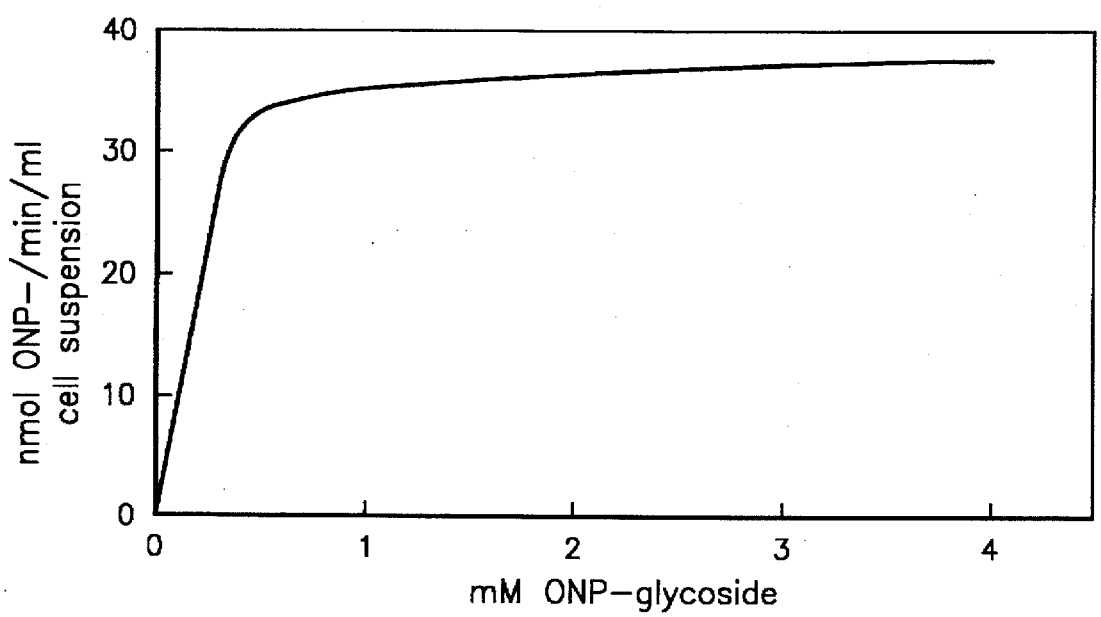

Looking more closely into the ONP-glycoside cleavage in dependency on substrate concentration, we find the presence of saturation kinetics without substrate inhibition (FIG. 4). By means of the Lineweaver-Burk process a maximal reaction velocity was registered during operation of 42 nmol/min/ml, as well as a $K_m$ value of 2 mM. Since, when increasing the substrate concentration, there was no further velocity increase to be registered, the dosage of the substrate to be used, according to the invention, takes place in accord with a cost and efficiency weighting at 2 mM. When performing the PTS inhibition test, in accordance with the invention, it also turned out that the sensitivity of the test is clearly dependent on the kind of buffer used. It was particularly conspicuous that phosphate buffer has a clearly stimulating effect on the ONP-glycoside hydrolysis, whereas, on the other hand, when performing the inhibition test with heavy metals as toxic substances, the strongest inhibitory effects were to be registered when using the HEPES buffer. It should however be taken into account that a phosphate buffer in the presence of heavy metal salts is less suitable due to solubility problems that then might occur. Therefore when testing heavy metals, the HEPES buffer should preferably be chosen.

Thus, the PTS inhibition test according to the invention will be carried out as follows:

The test occurs with a total reaction volume of 500 µl in Eppendorf cups, the O.D.$_{578}$ of the bacteria suspension amounting to 3.0.

The *E. coli* cultures of the mutant 1219 bgl+, preserved at −20° C., are first thawed to be reactivated during 10 min. at room temperature. They are then suspended in 250 µl of 50 mM buffer and together with the appropriate test solution and distilled water brought to a volume of 480 µl . This suspension is then pre-incubated over a time span of 10–15 minutes at 37° C. After that, the reaction is started by adding 20 µl of ONP-glucose (50 mM) (equivalent to a final concentration in the reaction batch of 2 mM). The reaction mixture is incubated over a time span of 5 minutes at 37° C. After the end of this reaction time the reaction is terminated by adding 1 ml of Na$_2$CO$_3$ (0.5M). After a 2 minute centrifugation at 17,000×g the substrate transformations of the tested bacteria suspensions are photometrically determined at 405 nm.

The evaluation of the PTS test with ONP-glycosides is done by means of the toxicological characteristic quantity of the "efficient concentration", (the EC value). It is hereinunder understood with such a concentration of added toxic substance that a measurable parameter of an organism will be inhibited to a certain extent within a freely defined time span. The percentage of adverse effect of the parameter to be measured is indicated by the attached index.

The conversion of the registered percentage inhibitory values into EC values is carried out with the help of the gamma method (Johnson, F. H., Eyring, H. and Stover, B. J., 1974; The theory of rate processes in biology and medicine, John Wiley & Sons, New York: 1–385). With the aid of the $O.D._{405}$, registered in the PTS inhibition test, the quotient is formed from the ONP-glycoside cleavage output and the remaining ONP-glycoside cleavage.

$$\text{Gamma} = \frac{D\ O.D._{405}}{O.D._{405} - D\ O.D._{405}}$$

$O.D._{405}$: Substrate transformation without toxic substance solution.

$D\ O.D._{405}$: Output of the substrate transformation after incubation with the toxic substance solution.

The gamma values hereby obtained are used against the employed concentration of toxic substance, in a double logarithmic representation. By plotting a straight regression line the EC values can then be established, the $EC_{10}$ value being had at the point of intersection between the straight line and the line parallel to the abscissa axis at a distance of 0.111, and the $EC_{50}$ value at a distance of 1.0.

The PTS inhibition test according to this invention will now be described in more detail, in the following examples, in conjunction with various toxic substances.

EXAMPLE 1

The PTS inhibition test with different heavy metals.

The test was conducted with the above-described batch in a HEPES buffer at pH 6.5. For example, for the inhibition through supply of $Hg^{2+}$ it was shown that the sensitivity of the test was more sensitive, by a factor of 50, when using a HEPES buffer instead of a phosphate buffer. When using the other buffers inhibitory effects of the metal ions did not appear until the concentrations were so high that precipitation occurred in the reaction batch (for instance $Cd^{2+}$ from approx. 500 ppm corresponding to 4.5 mM). To ensure the highest possible sensitivity of the test system, the examinations were performed in the PTS inhibition test on heavy metals in a HEPES buffer.

In the test solutions employed, different toxic substance concentrations of Cd-, Cr-, Cu-, Hg-, Ni- and Pb-salts (throughout as chlorides) were supplied, for which the inhibition is proportional to the concentrations applied. Inhibitory effects between 5% and 90% were registered. It was possible to dissolve all the heavy metal salts with the concentrations used in the HEPES buffer. Dose and effect relations (inhibition curves) were plotted, and the toxicologically relevant EC values were obtained through extrapolation. These indicate the concentration of the tested substance, at which the ONP-glycoside cleavage is inhibited for a certain figure in percentage terms, if standard values serve as a referential quantity, containing distilled water instead of the test solution.

To prevent the metal solution itself from being absorbed at 405 nm, appropriate control batches were measured, wherein the cell suspensions were replaced with buffers. Since the heavy metal ions were exclusively used as chloride, in addition, sodium chloride solutions were supplied as negative control, for the purpose of preventing a possible inhibition due to the anions.

In Table 4, the $EC_{10}$ and $EC_{50}$ values for the supplied heavy metal ions are represented, respectively, with the concentration data in ppm, which is commonplace in the ecotoxicology, and in µM units which is commonplace in biochemistry.

TABLE 4

| Metal Ion | $EC_{10}$ ppm | $EC_{10}$ µM | $EC_{50}$ ppm | $EC_{50}$ µM |
|---|---|---|---|---|
| $Cd^{2+}$ | 10 | 89.0 | 19 | 169.1 |
| $Cr^{3+}$ | 8 | 153.6 | 16 | 307.2 |
| $Cu^{2+}$ | 5.5 | 86.4 | 11 | 172.7 |
| $Hg^{2+}$ | 1.3 | 6.4 | 2.1 | 10.3 |
| $Ni^{2+}$ | 0.5 | 8.5 | 4.5 | 76.6 |
| $Pb^{2+}$ | 25 | 120.0 | 67 | 321.6 |
| $Zn^{2+}$ | | | 8 | 122.4 |

It can be seen in Table 4 that the hydrolysis of the ONP-glucose reacts the most sensitively to the presence of $Ni^{2+}$ and $Hg^{2+}$. Already 0.5 ppm $Ni^{2+}$ (equivalent to 8.5 µM) and 1.3 ppm $Hg^{2+}$ (equivalent to 6.4 µM) give rise to a 10% inhibition. The $EC_{50}$ value of $Ni^{2+}$ is with 4.5 ppm (equivalent to 76.6 µM) higher than the corresponding $EC_{50}$ value of $Hg^{2+}$ with 2.1 ppm (equivalent to 10.3 µM). With both of the metal ions a maximal inhibition of about 70% was achieved.

With the exception of $Pb^{2+}$, which with an $EC_{50}$ value of 67 ppm (equivalent to 321.6 µM) exerted the weakest inhibitory effect on the *E. coli* mutant that was used, the resulting $EC_{10}$ and $EC_{50}$ values of $Cu^{2+}$, $Cr^{3+}$ and $Cd^+$ having 5.5 ppm–10 ppm ($EC_{10}$) and 11 ppm–19 ppm ($EC_{50}$), respectively, are in a relatively narrow proximity to each other. The relations, however, are different when substance-amount concentrations are given (µM): $Cr^{3+}$ inhibits first at a higher molar concentration (153.6 µM) than $Pb^+$ (120 µM), although the corresponding $EC_{10}$ value of 25 ppm, for $Pb^{2+}$, is more than three times greater than for $Cr^{3+}$ with 8 ppm.

EXAMPLE 2

The PTS inhibition test with organic solvents.

The water-insoluble solvents chloroform, phenol and toluene as well as the water soluble dioxan and ethanol were used as test substances. Since water-insoluble solvents had to be tested, an aqueous phase was used that was saturated with these solvents. For the purpose, the water-insoluble solvents were first entered into distilled water, and the aqueous phase was saturated overnight, under constant agitation, with the respective solvent. The concentrations of the aqueous phases, on water-insoluble solvent amounted to 0.81% (v/v) for chloroform, 8.2–9.2% (v/v) for phenol and 0.074% (v/v) for toluene. These aqueous phases saturated with solvents were then supplied to the cell suspensions in different thinning or dilution stages.

As buffer system served a 50 mM phosphate buffer at pH 6.5, since it was thereby possible during inhibition of the ONP-glucose cleavage to achieve an increase of the sensitivity by up to 20% relative to the other buffer systems. The other parameters: incubation time, reaction time, bacteria quantity, temperature and substrate concentration were set in accordance with the values of Example 1.

The toxicologically relevant EC values were obtained as in Example i from dose/effect relations (inhibition curves) through extrapolation (gamma method). In FIG. 2, the inhibition straight lines are again shown in a double logarithmical representation. The resulting $EC_{10}$ and $EC_{50}$ values are given in Table 5.

TABLE 5

| Solvent | EC$_{10}$ ppm | EC$_{10}$ µM | EC$_{50}$ ppm | EC$_{50}$ µM |
|---|---|---|---|---|
| Chloroform | 720 | 6.0 | 1,900 | 15.9 |
| Phenol | 350 | 3.7 | 1,400 | 14.9 |
| Toluene | 15 | 0.16 | 35 | 0.38 |
| Dioxan | 10,000 | 114 | 30,000 | 341 |
| Ethanol | 10,500 | 288 | 33,000 | 717 |

As can be seen in the Table, most of the organic solvents that were used exert inhibitory effects on the ONP-glucose transformation of *E. coli* first when in high concentrations. It was only toluene that, among the water-insoluble solvents, gave rise to obvious inhibitions already when in small amounts. The EC$_{10}$ value was registered at 15 ppm (equivalent to 0.16 µM) and, thus, was almost by a factor of 50 below the corresponding value for chloroform, which effected an ONP-glucose transformation output of 10% not until at 720 ppm (approx. 6 µM). In addition, there were also attempts made to determine the effect of dichloroethane on the ONP-glucose transformation, but no extrapolation to the needed gamma values was possible. Dichloroethane was supplied to a concentration of approx. 3,500 ppm. This corresponds to an approximative 35 µM concentration of amount of substance, at which only an inhibition of about 30% could be achieved.

The water soluble solvents dioxan and ethanol exert little effects on the ONP-glucose hydrolysis. The EC$_{10}$ values amounted to approx. 10,000 ppm for dioxan and approx. 10,500 ppm for ethanol, which corresponds to a substance-amount concentration of 0.11 mol/l and 0.28 mol/l, respectively.

EXAMPLE 3

The PTS inhibition test with detergents.

The ionic detergent SDS and the non-ionic Triton X-100 were examined as detergents in their effect on the PTS system of *E. coli* 1219 bgl+. As buffer system served a 50 mM HEPES buffer at pH 6.5. The remaining reaction parameters corresponded once again to the values of Example 1.

The extrapolation of the transformation rates resulted, upon incubation with SDS, in an EC$_{10}$ value of 5.5 ppm, corresponding to a substance-amount concentration of about 19 µM, and in an EC$_{50}$ value of 13 ppm, corresponding to 45.1 µM. The non-ionic Triton X-100 showed first in higher concentrations a significant inhibition, corresponding to an EC$_{10}$ value of about 70 ppm (equivalent to 108 µM) and to an EC$_{50}$ value of about 180 ppm (equivalent to about 280 µM). The values are once again summarized in Table 6.

TABLE 6

| Detergent | EC$_{10}$ ppm | EC$_{10}$ µM | EC$_{50}$ ppm | EC$_{50}$ µM |
|---|---|---|---|---|
| SDS | 5.5 | 19.1 | 13 | 45.1 |
| Triton X-100 | 70 | 108 | 180 | 278 |

In order to elucidate the performance capability of the PTS inhibition test according to the invention, the data that was registered in the Examples are presented, in the following Table 7, in juxtaposition with the data registered with the bioluminescence inhibition test according to DIN 384 12, part 34.

TABLE 7

| Test Substance | PTS Inhibition Test EC$_{50}$ (ppm) | Reaction Time In Min. | Bioluminescent Inhibition Test EC$_{50}$ (ppm) | Reaction Time In min. | Reference |
|---|---|---|---|---|---|
| Cd$^{2+}$ | 19 | 5 | 131 | 10 | Beckmann, 1980 |
| Cu$^{2+}$ | 11 | 5 | 16 | 10 | Beckmann, 1980 |
| Zn$^{2+}$ | 8 | 5 | 25.4 | 10 | Beckmann, 1980 |
| Hg$^{2+}$ | 2.1 | 5 | 0.065 | 5 | Bulich et al., 1981 |
| Pb$^{2+}$ | 67 | 5 | 0.4 | 30 | Beckmann, 1981 |
| Chloroform | 1,900 | 5 | 1,168 | 10 | Beckmann, 1980 |
| Phenol | 1,400 | 5 | 25 | 5 | Bulich et al., 1981 |
| Ethanol | 33,000 | 5 | 31,000 | 5 | Bulich et al., 1981 |

*Beckmann, 1980: The microtax system, an approach to acute water toxicity monitoring. - Microtax slide presentation; Beckmann Instruments Inc.; Microbic Operations, Carlsbad, Calif., USA.
Bulich, A. A., Green, M. W. and Isenberg, D. L., 1981; Reliability of the bacterial luminescence assay for determination of the toxicity of pure compounds and complex effluents. In: Branson, D. R. and Dickson, K. L. (eds.): Aquatic toxicology and hazard assessment: fourth conference. ASTM STP 737:338–347.

In the comparison of corresponding inhibition data for the heavy metal ions Cd$^{2+}$, Cu$^{2+}$ and Zn$^{2+}$, it is evident that the PTS test according to the invention reacts substantially in a more sensitive way than the bioluminescent inhibition test, in particular when it is also taken into account that the reaction time of 5 minutes only amounts to about half the reaction time of the bioluminescent inhibition test. This is particularly evident in regard to the respective EC values, which are registered after incubation with Cd$^{2+}$. In the PTS inhibition test a 50% inhibition was achieved already by 19 ppm of Cd$^{2+}$. When considering that the substrate transformation is proportional to the reaction time, then the test according to the invention is more sensitive, by a factor of 14, than the bioluminescent inhibition test, in which it was possible to register a corresponding inhibition at a concentration of 131 ppm after a reaction time of 10 minutes. In addition, the test according to this invention constitutes a sensitive inhibition test for Cr$^{3+}$ with an EC$_{50}$ value of 16 ppm. In the literature such data has not been found with the bioluminescent inhibition test.

The presence of Pb$^{2+}$ and Hg$^{2+}$, however, has a clearly more insensitive impact on the ONP-glucose transformation than in the bioluminescent inhibition test. For the organic solvents chloroform and ethanol, on the other hand, the achieved sensitivities are approximately of the same magnitude. For phenol, however, the bioluminescent inhibition test proves to be clearly more sensitive.

A comparison of the EC values with regard to detergents with the bioluminescent inhibition test was not possible due to lack of literature data. Both the cationic SDS and the non-ionic Triton X-100 showed significant inhibitions, in the PTS inhibition test, at relatively low concentrations. The EC$_{10}$ values were registered for SDS at 5.5 ppm and for Triton X-100 at 70 ppm, and were therefore within the magnitude of the inhibitory rates for heavy metals.

The PTS test according to the invention represents as far as its handling is concerned a test system that is easy to perform. Because of the possibility to use frozen bacteria the test is performable without preparation. With the above-described preservation method for the bacteria cultures to be used, it is possible to arrange test organisms for as many tests as desired. Since the actual inhibition test is separate from the cultivation of microorganisms, no sterile workplace is required for the test implementation and the test can be conducted with standard laboratory equipment (centrifuge, photometer, temperature control water baths). Thus, the process according to this invention provides an extremely desirable test especially because of its high sensitivity vis-à-vis the heavy metal ions $Cd^{2+}$, $Cu^{2+}$, $Zn^{2+}$ and, in particular, also vis-à-vis $Cr^{3+}$, thereby closing up a lacuna with regard to tests known in the State of the Art for the detection of toxic substances.

What is claimed is:

1. A process for detection of toxic substances wherein said process involves determining the inhibition effect of such toxic substances, contained in a sample, on microorganism metabolism, wherein the inhibition effects of the toxic substances on carbohydrate transport into the microorganism, as effected by the microorganism phosphotransferase systems, are determined and serve as evidence of toxic substances being present in the sample, wherein said process comprises:

producing a suspension of bacterium cells having said phosphotransferase system along with the sample to be examined, in a buffer system;

adding a substrate analog for a carbohydrate, wherein the substrate analog is transported into the bacterium cells by means of the phosphotransferase systems, which is dependent on a phosphoenol pyruvate, under phosphorylation, wherein the substrate analog, after its phosphorylation, is hydrolyzed by a bacteria specific enzyme of the phosphotransferase system thereby releasing a substance susceptible to analysis;

determining the released substance concentration after a defined reaction time; and comparing the determined concentration of the released substance with a value obtained from a comparative batch of a suspension without a sample additive.

2. The process of claim 1, wherein the concentration of the released substance is determined photometrically.

3. The process of claim 1, wherein the substrate analog is a 2-nitrophenyl-glycoside or a 4-nitrophenyl-glycoside.

4. The process of claim 3, wherein the 2-nitrophenyl-glycoside is 2-nitrophenyl-β-D-glucoside and wherein the 4-nitrophenyl-glycoside is 4-nitrophenyl-β-D-glucoside.

5. The process of claim 4, wherein the process further comprises: incubating the suspension, after adding the substrate analog, for about 5 minutes at about 37° C. for hydrolysis of the 2-nitrophenyl-β-D-glucoside or the 4-nitrophenyl-β-D-glucoside.

6. The process of claim 5, wherein the process further comprises: terminating the hydrolysis of the 2-nitrophenyl-β-D-glucoside or the 4-nitrophenyl-β-D-glucoside by adding an effective quantity of a 0.5M $Na_2CO_3$ solution.

7. The process of claim 6, wherein the process further comprises: centrifuging off the bacterium cells after termination of the hydrolysis at about 17,000×g for about 2 minutes, and determining the remaining 2-nitrophenolate or anion 4-nitrophenolate anion concentration photometrically at 405 nm.

8. The process of claim 1, wherein the bacterium cells comprise a mutant of E. coli deposited with DSM-DEUTSCHE SAMMLUNG VON MIKROORGANISMEN UND ZELLKULTUREN GmbH and having an identification reference of 1219bgl+ and a deposit number of DSM 8779.

9. The process of claim 8, wherein the bacteria mutant E. coli 1219 is present in a quantity sufficient to enable the bacteria suspension to render an optical density reading at 578 nm ($OD_{578}$) equal to about 3.0.

10. The process of claim 1, wherein the process further comprises: freezing bacteria cultures down to about −20° C., and then thawing the bacteria cultures before adding the cultures or growths of bacterium cells to the suspension.

11. The process of claim 10, wherein the process further comprises: washing the bacterial cultures with a 10% bovine serum albumin solution before freezing the cultures.

12. The process of claim 10, wherein thawing the bacteria cultures comprises thawing the frozen bacteria cultures at room temperature for about 10 minutes, and then preincubating the bacteria cultures for about 10 to 15 minutes at about 37° C. in a buffer system suitable for physiological purposes and having a pH between about 6 and about 8.5 prior to adding the bacteria cultures to the suspension.

13. The process of claim 1, wherein a 50 mM HEPES buffer with a pH of about 6.5 is used as the buffer system.

14. The process of claim 1, wherein a 50 mM phosphate buffer with a pH of about 6.5 is used as the buffer system.

* * * * *